United States Patent [19]
Zuroski

[11] Patent Number: 5,513,266
[45] Date of Patent: Apr. 30, 1996

[54] INTEGRAL ACTIVE AND PASSIVE SILENCER

[75] Inventor: Michael T. Zuroski, Sun Prairie, Wis.

[73] Assignee: Digisonix, Inc., Middleton, Wis.

[21] Appl. No.: 236,565

[22] Filed: Apr. 29, 1994

[51] Int. Cl.⁶ .............................. A61F 11/06; H03B 29/00
[52] U.S. Cl. .............................. 381/71; 381/94; 415/119; 181/224
[58] Field of Search ................... 381/71, 94; 415/119; 181/224, 222, 252, 258

[56] References Cited

U.S. PATENT DOCUMENTS

| | | |
|---|---|---|
| 4,359,136 | 11/1982 | Eriksson . |
| 4,665,549 | 5/1987 | Eriksson et al. . |
| 4,969,536 | 11/1990 | Allen ........................................ 415/119 |
| 5,044,464 | 9/1991 | Bremigan . |
| 5,088,575 | 2/1992 | Eriksson .................................. 381/71 |
| 5,229,556 | 7/1993 | Geddes . |
| 5,233,137 | 8/1993 | Geddes . |
| 5,272,286 | 12/1993 | Cain ......................................... 381/71 |

*Primary Examiner*—Curtis Kuntz
*Assistant Examiner*—Minsun Oh
*Attorney, Agent, or Firm*—Andrus, Sceales, Starke & Sawall

[57] ABSTRACT

An integral active and passive silencer particularly useful for industrial applications. The integral unit is easy to install, disassemble and service. It provides a housing that can be separated into portions, with each portion containing an active or passive silencer. The invention also provides an active silencer having a ported tube that is in acoustic communication with one or more loudspeakers through a tuning chamber. The ported tube can be removable.

44 Claims, 5 Drawing Sheets

INTEGRAL ACTIVE AND PASSIVE SILENCER

FIELD OF THE INVENTION

The invention relates to acoustic silencers incorporating active and passive silencing components. More specifically, the invention is such a silencer in which active and passive components are packaged in an integral unit that is easy to install, disassemble and service. The invention is particularly useful for industrial silencing applications.

BACKGROUND OF THE INVENTION

Passive silencers are conventionally used in many industrial applications to reduce sound propagating through pipes or ducts. Passive silencers can have baffles, acoustic expansion chambers, and/or acoustically adsorptive material, and typically work well at high to middle acoustic frequencies, but perform less effectively when frequencies drop below 500 Hertz. Baffles improve the performance of passive silencers, but severely restrict air or gas flow through the silencer. Flow restrictions are undesirable in many industrial applications because the flow restrictions often cause inefficiencies elsewhere in the industrial process.

In contrast to passive silencers, active sound control systems perform best on low frequency sound waves that have relatively long wavelengths. Also, in general, active systems do not restrict flow significantly. Active sound control systems cancel input acoustic waves propagating down a pipe by introducing a canceling acoustic wave to destructively interfere with the input acoustic waves so that the amplitude of output acoustic waves exiting from the pipe are reduced. It is typical to sense input acoustic waves with one or more input transducers (e.g. input microphones) and sense output acoustic waves with one or more error transducers (e.g. error microphones). The input transducers supply input signals to an electronic controller, and the error transducers supply error signals to the electronic controller. The electronic controller is programmed to model the acoustics in the pipe and filter the signals from the transducers (e.g. microphones) to generate a correction signal. The correction signal is supplied to an actuator (e.g. a canceling loudspeaker); and, in response to the correction signal, the actuator introduces the canceling acoustic wave to destructively interfere the input acoustic waves propagating down the pipe.

Since active sound control systems perform better at low frequencies and passive silencers perform better at middle to high frequencies, it is desirable to combine active and passive silencing components in a single unit to improve performance over a broad band of acoustic frequencies. The silencing requirements at various industrial applications can be extremely inconsistent, however, as can be the amount of allowable flow restriction. It is, therefore, desirable that such a combined active and passive silencer be easy to retrofit to match the needs of the industrial application in which it is used. It is further desirable that such a combined active and passive silencers be tightly packaged, and easy to install, disassemble and service.

SUMMARY OF THE INVENTION

In one aspect, the invention is a combined active and passive acoustic silencer having an outer housing with a front and a rear portion, and a passive silencer located in the front portion and an active silencer in the rear portion. The active silencer has an actuator for generating a canceling acoustic wave. The actuator is in acoustic communication with the flow of gas through the housing through a port in a tube that is located in the rear portion of the housing. The tube can be removable.

In another aspect, the invention is a combined active and passive acoustic silencer having an outer housing that can be easily separated into a rear portion and a front portion. When installed, the front and the rear portions of the housing are attached together so that the combined active and passive silencer forms an integral unit. This configuration makes the silencer easy to disassemble and service.

In particular, the preferred acoustic silencer has an outer housing with an inlet for receiving a gas flowing through a pipe and an outlet through which the gas exits the housing. The inlet is in a front portion of the housing and the outlet is in a rear portion of the housing. The front portion is physically separate from the rear portion. The front and rear portions of the housing have outwardly extending flanges so that the front and rear portions can be connected together using nuts and bolts. A passive silencer is located in the front portion of the housing, and an active silencer is located in the rear portion of the housing. The active silencer has a tube through which gas flows from the passive silencer in the front portion to the outlet in the rear portion. The tube has a port and is preferably removable. An actuator (e.g., a loudspeaker) generates a canceling acoustic wave that is preferably tuned to a preferred band width in a tuning chamber that provides acoustic communication between the actuator and the port in the tube. It is preferred that the active silencer have an error transducer that senses sound downstream of the port in the tube. It is also preferred that the active silencer have an input transducer located in the front portion of the housing.

The preferred silencer should have two actuators or loudspeakers in the rear housing portion, and each speaker should have a diaphragm facing the tuning chamber. It is preferred that each diaphragm be located symmetrically opposite to the other diaphragm and move substantially perpendicular to the longitudinal axis of the silencer. The two-speaker configuration helps prevent unwanted vibrations. When an active silencer in the present invention uses a tuning chamber and a ported tube, it is preferred that the ported tube be removable and that the tuning chamber having sufficient dimensions so that the speakers can be removed through the tuning chamber when the ported tube is not in the tuning chamber.

In another embodiment of the invention, the outer housing has a middle portion in addition to the front and rear portions. The middle portion is also separable from the front and rear portions. Another passive silencer or another active silencer can be located in the middle portion depending on the needs of the particular application. The additional active or passive silencer that is located in the middle portion is preferably adapted to attenuate sound in a frequency band in which the silencers in the front and rear portions are not sufficiently effective. For instance, an active silencer in the middle portion could have speakers with a different frequency band than the speakers in the rear portion, or the dimensions of the tuning chamber or the port in the tube in the middle portion could be modified to redistribute speaker power to a different frequency band.

In another aspect of the invention, electrical connections for the active silencers are made in a manner that makes the combined silencer easy to install, operate, and retrofit. For example, the invention provides a wiring system in which all necessary electrical connections for active silencing to an electronic controller can be made by plugging a single socket connector into a single socket located in the housing of the silencer.

In yet another aspect, the invention is an active acoustic silencer having a housing with an inlet and an outlet, and an actuator and a removable, ported tube within the housing.

It is therefore an object of the invention to provide an acoustic silencer having improved performance over a broad band of acoustic frequencies. The present invention achieves this object by combining passive and active silencing into an integral silencer.

Another object of the present invention is to provide such a silencer that is easy to install. The invention achieves this object by providing an integral system having a single input to receive the flow of fluid through which sound is propagating, a single output for outputting the flow of fluid, and a single electrical connection to an electronic controller.

Another object is to provide such a combined silencer that is easy to service. The invention achieves this object by providing an active portion that is physically separable from a passive portion, and providing a silencer structure that is easily accessible once the portions are separated.

Another object is to provide a silencer that does not severely restrict the flow of fluid through the silencer. The invention achieves this object by using a bullet-like passive silencer, and locating the speakers in the active portion out of the flow path for the fluid.

Another object is to provide a combined silencer without using large speakers or excessive speaker amplifiers. The invention achieves this object by using a ported tuning chamber to improve speaker efficiencies at low frequencies.

Yet another object of the present invention is to provide a combined silencer that can accommodate an additional active and/or passive silencing component if needed to improve silencer performance. The invention achieves this object by providing a modular structure wherein the various active and passive portions are physically separable from one another.

Other objects and advantages will appear in the course of the following description.

DETAILED DESCRIPTION OF THE PREFERRED EMBODIMENT

Figure 7:
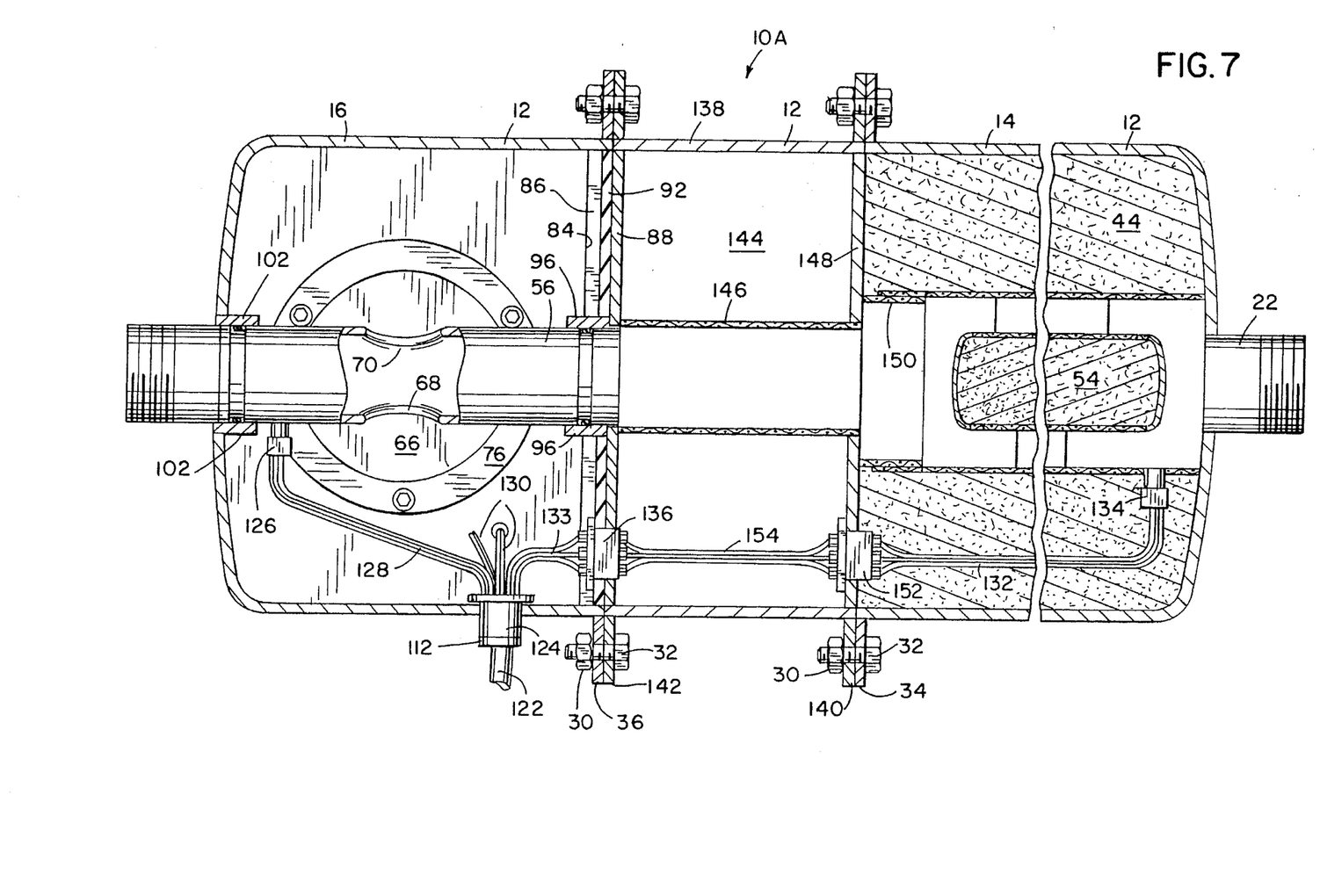
FIG. 7 is a longitudinal sectional view of another embodiment of an acoustic silencer made in accordance with the invention.

A first embodiment of an acoustic silencer 10 in accordance with the present invention is shown in FIGS. 1 through 5. A second embodiment of an acoustic silencer 10A is shown in FIG. 7, and a third embodiment of an acoustic silencer 10B shown in FIG. 8. Each of these acoustic silencers 10, 10A and 10B are particularly well suited for silencing sound propagating through a gas or air flow in an industrial application. Each of the acoustic silencers 10, 10A and 10B are compact, easy to install, disassemble and service, and easy to operate. Furthermore, as will be apparent from the following description, these acoustic silencers 10, 10A, 10B are preferably constructed so that the various components are physically compatible. This physical compatibility means that the acoustic silencers 10, 10A and 10B are easy to reconfigure to match the acoustic requirements of the particular application. This flexibility is important because the performance requirements of an acoustic silencer can change from installation to installation, and can even change after the silencer is initially installed.

Figures 1, 3, 6:
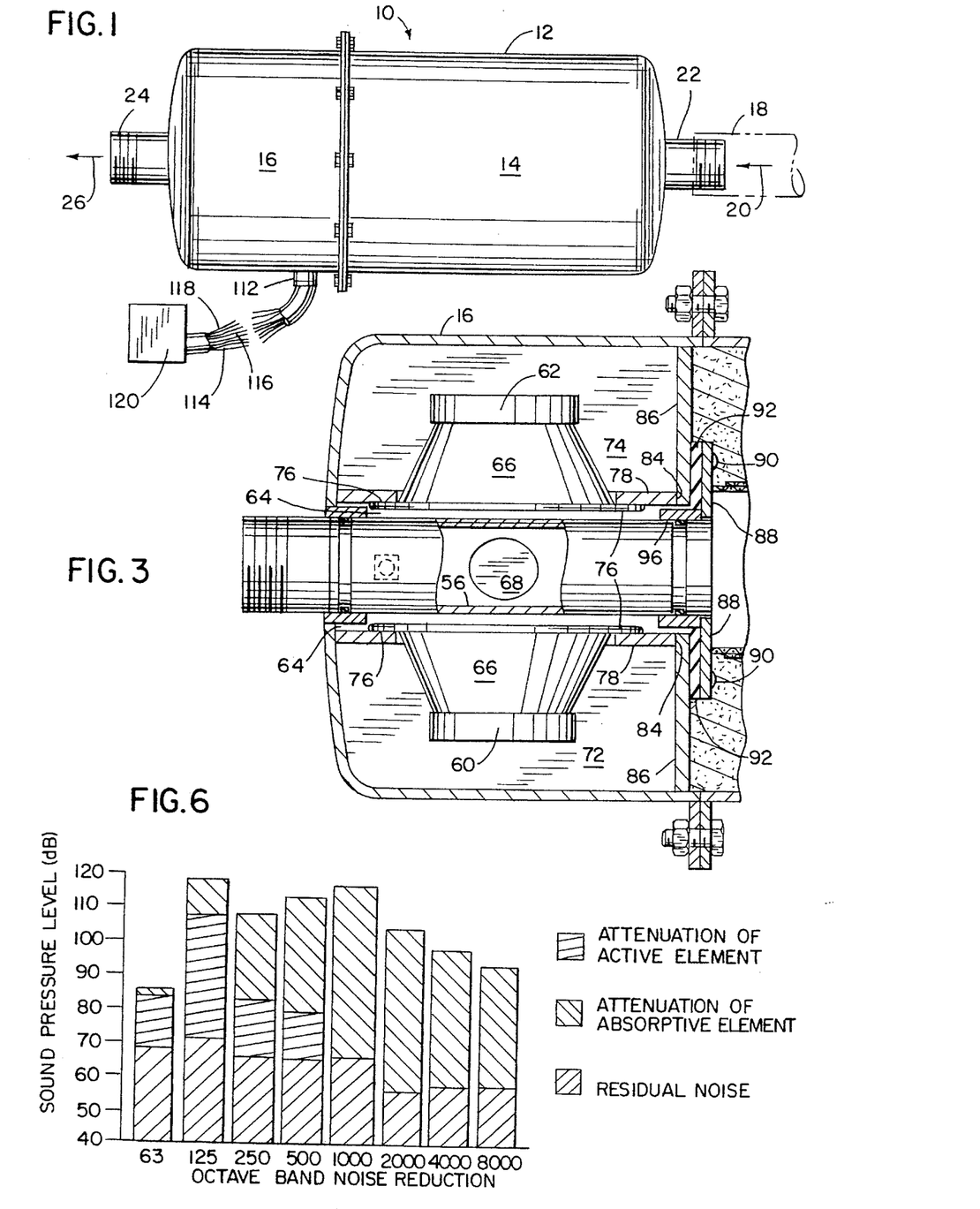
FIG. 1 is a side elevational view of an embodiment of an acoustic silencer in accordance with the invention.
FIG. 3 is a longitudinal sectional view taken along line 3—3 in FIG. 2.
FIG. 6 is a plot of data showing the performance of the acoustic silencer shown in FIG. 1.
Figure 2:
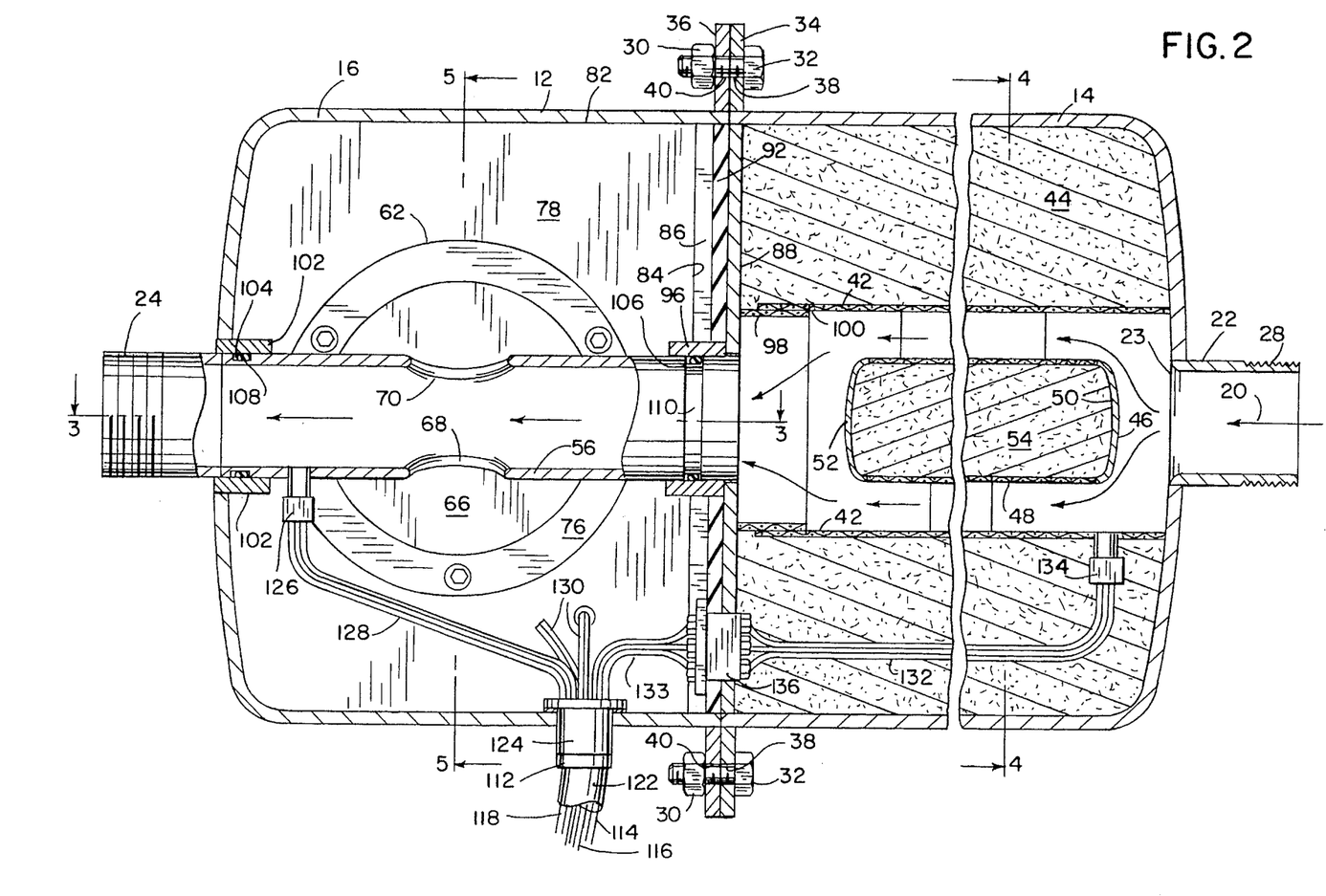
FIG. 2 is a sectional view taken along a longitudinal axis of the acoustic silencer in FIG. 1.

Referring to FIGS. 1 and 2, the acoustic silencer 10 has an outer housing 12 that is separated into a front portion 14 and a rear portion 16. Gas flowing through a pipe 18 (shown in phantom in FIG. 1) in the direction of arrows 20 flows into the front portion 14 of the outer housing 12 through an inlet 22. In most applications, the gas will be air or exhaust gases, but the invention is not limited to silencing sound in these gases. The gas flows through the acoustic silencer 10 and exits through an outlet 24 located in the rear portion 16 of the outer housing 12. Sound propagating through the gas flow in the pipe 20 is silenced or attenuated as it flows through the acoustic silencer 10 so that the sound level in the gas flow 26 after it exits the outlet 24 is reduced.

Referring to FIG. 2, the inlet 22 has an inside diameter that is compatible with the pipe 18 through which the gas is received. For common industrial applications, the inlet 22 will probably have a 2" inside diameter. The inlet 22 has male pipe threads 28 to facilitate installation with the pipe 18 which would normally have female pipe threads. It is further preferred that the inside edge 23 of the inlet 22 be rounded to smooth air flow. Likewise, it is preferred that the outlet 24 have an inside diameter and threads that are compatible with a pipe into which the gas 26 exits. It is anticipated that the pipe 18 at the inlet and the pipe at the outlet will have the same dimensions, so it is preferred that the outlet 24 have an inside diameter of 2", and also have male threads like threads 28 as shown on the inlet 22.

The front portion 14 of the outer housing 12 can be physically separated from the rear portion 16 of the outer housing 12. The front portion 14 and the rear portion 16 are connected together using nuts 30 and bolts 32 through a flange in the front portion and a flange in the rear portion to form an integral unit when the silencer 10 is installed for operation. The front portion 14 has a peripheral flange 34 extending outward from the front housing portion. The peripheral flange 34 preferably extends around the entire circumference of the front portion 14. Likewise, the rear portion 16 has a flange 36 extending outwardly from the front edge of the rear portion 16. The flange 36 on the rear portion 16 preferably extends around the entire circumference of the rear portion 16. The flange 34 of the front portion 14 has several holes 38, and the flange 36 of the rear portion 16 has several holes 40. To connect the front portion 14 to the rear portion 16, the holes 38 and 40 are lined up, bolts 32 are passed through the holes 40 and 38, and the nuts 30 are tightened onto the bolts 32.

A bullet-type passive silencer is located in the front portion 14 of the housing 12. The bullet-type passive silencer has a perforated metal cylinder 42 coaxial with the longitudinal axis of the silencer 10. The diameter of the cylinder 42 is larger than the diameter of the inlet 22. The perforated metal cylinder 42 is acoustically permeable. Acoustic packing material or other acoustically absorptive material 44 is packed around the cylinder 42 between the cylinder 42 and the front portion 14 of the outer housing 12. A bullet-like member 46 is located coaxially within the perforated metal cylinder 42. The bullet-like member 46 has a cylindrical wall 48 made of perforated metal and is positioned coaxially along the longitudinal axis of the silencer 10. The bullet-like member 46 also has a front plate 50 and a rear plate 52 which cap the ends of the bullet cylinder 48. The front plate 50 and the rear plate 52 are preferably made of metal that is not perforated. The bullet 46 is packed with acoustic packing material 54, or some other acoustically absorptive material.

Figure 4:
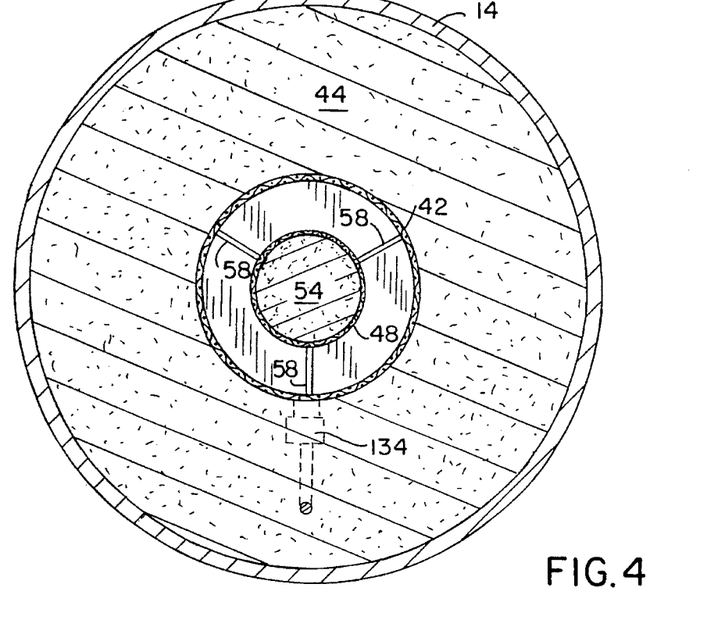
FIG. 4 is a cross sectional view taken along line 4—4 in FIG. 2.

Referring to FIG. 4, the bullet-like member 46 is supported coaxially within the perforated metal cylinder 42 by radial spokes 58 spanning between the cylindrical wall 48 of the bullet 46 and the perforated metal cylinder 42. It is preferred that the cross sectional area of the flow space between the perforated cylindrical wall 42 and the perforated cylindrical wall 48 of the bullet-like member 46 be equal to or greater than the cross sectional area of the flow through the inlet 22.

As the gas flows through the bullet-type passive silencer shown in FIG. 2, sound propagating through the gas flow is attenuated by the acoustic packing material 44 and 54. As can be seen in FIG. 6, the bullet-type passive silencer located in the front portion 14 of the silencer 10 is quite effective at attenuating middle to high frequency sound, but is not as effective for attenuating sound at lower frequencies.

It is preferred to use a bullet-type passive silencer as shown in FIG. 2 in the front portion 14 of the acoustic silencer 10, although other types of passive silencers may be used depending on the particular application. The bullet-type passive silencer is preferred because bullet-type silencers create relatively low resistance to the flow of gas (i.e. no flow reversal). A straight through type of passive silencer would have less resistance to flow, but might not perform as well as a bullet-like silencer. For instance, a straight through silencer would need to be longer. On the other hand, a normal baffled muffler might have better low frequency performance, but would severely restrict flow.

After the gas flows through the bullet-like passive silencer in the front portion 14, it flows into a ported tube 56 located in the rear portion 16 of the housing 12. The remaining sound is actively attenuated as the sound propagates through the tube 56 in the rear portion 16 of the housing 12. Referring to FIG. 3, loudspeakers 60 and 62 are mounted within the rear portion 16 of the housing 12 and generate a canceling acoustic wave that actively attenuates sound propagating through the tube 56.

The ported tube 56 is located in an acoustically sealed tuning chamber 64. Each speaker 60 and 62 has a diaphragm facing the tuning chamber 64. A diaphragm 66 for speaker 62 is shown in FIG. 2. The ported tube 56 has two ports 68 and 70, and the diaphragms 66 for speakers 60 and 62, are in acoustic communication with the flow of gas through the tube 56 via the tuning chamber 64 and the ports 68 and 70. It is preferred that the ports 68 and 70 open in a direction orthogonal to the direction that the speaker diaphragms face. It is also preferred that the edges of the ports 68 and 70 be rounded for smoother air flow (e.g., ⅛" radius for ¼" width of tube 56). Likewise, the upstream edge (not shown) of the tube 56 is rounded on the inside for the same reason.

Proper dimensioning of the ports 68 and 70, the tuning chamber 64 and the enclosed volumes 72 and 74 behind the speakers 60 and 62 enables effective active silencing at low frequencies with smaller speakers 60 and 62. In other words, proper dimensioning provides resonant frequencies within the bandwidth that most needs to be attenuated by the active silencer so that smaller speakers can be used. Thus, a properly tuned active silencer can be more compact.

In the preferred system, the speakers 60 and 62 are 8 ohm speakers that have a power output in the 50 to 700 Hz range. The tuning chamber 64 has a total volume of 4.2 liters. The enclosed volumes 72 and 74 behind the speakers 60 and 62 are each 2.5 liters. The ports 68 and 70 have a 1¼" radius, and the width of the tube 56 is ¼" so the length of the ports 68 and 70 is ¼". With these specifications, the speaker output power is tuned between 80 and 300 Hz, which is the band width in which most of the acoustic power for active attenuation is required in normal applications. Analysis has shown that reducing the volume 72 and 74 behind speakers 60 and 62 can increase the axial load on the speakers 60 and 62 and reduce efficiencies particularly at lower frequencies within the tuned band width.

Each speaker 60 and 62 is mounted symmetrically opposite to the other speaker around the longitudinal axis of the silencer 10. The speaker diaphragms operate in unison so as not to change the center of mass. Such a configuration with two speakers 60 and 62 eliminates vibration of the housing 12 that could occur if only a single speaker was used.

Figure 5:
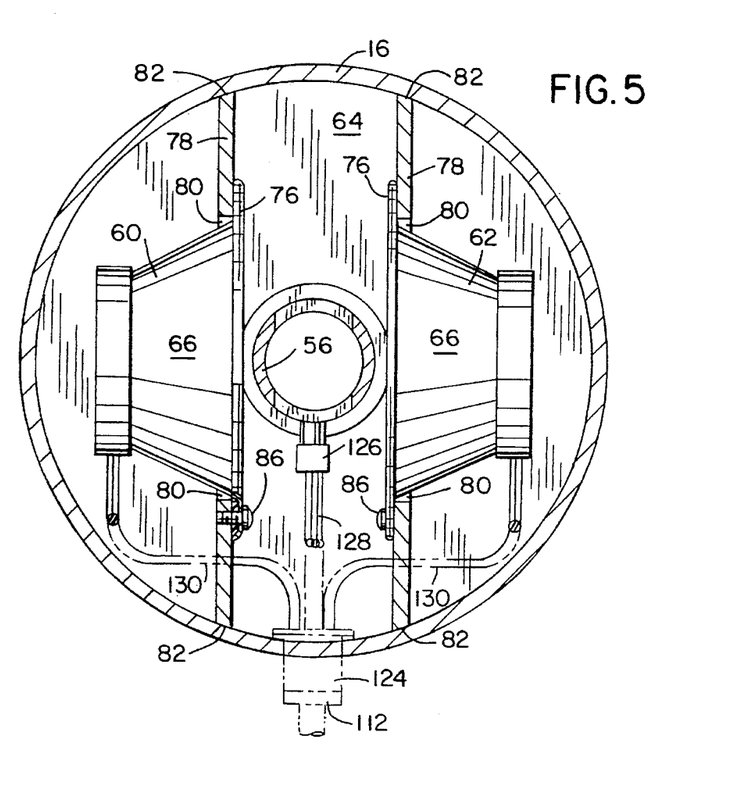
FIG. 5 is a cross sectional view taken along line 5—5 in FIG. 2.

Referring in particular to FIGS. 3 and 5, the mounting arrangements for the speakers 60 and 62 are now explained in more detail. Each speaker 60 and 62 has a rigid frame 76 to which the diaphragm 66 is attached. The frames 76 are each mounted to a separate speaker mounting plate 78. Each speaker mounting plate 78 has a peripheral edge and a part of the peripheral edge 82 is attached to the rear portion 16 of the housing 12. A part 84 of the peripheral edge of the speaker mounting plate 78 that faces the front portion 14 of the housing 12 is not attached to the rear portion 16 of the housing 12. Each speaker mounting plate 78 has a speaker hole 80 therein. The hole 80 in the speaker mounting plate 78 is larger than the diaphragm 66 but it is not larger than the frame 76. The speakers 60 and 62 are each mounted by screwing the speaker frame 76 to the speaker mounting plate 78 in such a manner that the frame 76 and the head of the screw 86 are exposed to the tuning chamber 64. It is preferred that the distance between the mounting plates 78 be large enough so that the speakers 60 and 62 can be removed through the tuning chamber 64 when the ported tube 56 is removed from the rear portion 16 of the housing 12.

Referring now to FIGS. 2 and 3, volumes 72 and 74 behind the speakers 60 and 62, respectively, are enclosed with an enclosure plate 86. A curved edge at the enclosure plate 86 is attached to the rear portion 16 of the outer housing and a straight edge of the enclosure plate 86 is attached to the part 84 of the peripheral edge of the speaker mounting plate 78 that is not attached to the housing 16. The volumes 72 and 74 are sealed. Silicone may be necessary for proper sealing. Since the speaker back volumes 72 and 74 are enclosed and sealed, speaker components such as the magnets are protected from the flow of gas through the silencer 10. Also, sound is not allowed to propagate from the rear side of the diaphragm 66 to the outside of the silencer 10.

A cover plate 88 spans between the enclosure plates 86 to acoustically seal the tuning chamber 64. The cover plate is screwed to the enclosure plates 86 using screws 90. The heads of the screws 90 are exposed towards the front of the silencer 10 so that the screws can be accessed when the front 14 and rear 16 portions are separated. A rubber gasket 92 is located between the cover plate 88 and the enclosure wall 86 to improve the acoustic seal. The cover plate 88 has a hole 94 that allows gas to flow through the cover plate 88. The inside diameter of the hole 94 of the cover plate 88 is roughly the same as the inside diameter of the inlet 22. The cover plate 88 has a cylindrical collar 96 around the hole 94 that extends rearward. The collar 96 supports the ported tube 56. It is preferred that the cover plate 88 also have another collar 98 extending towards the front of the silencer 10 that is made of perforated metal. The collar 98 extending toward the front of the silencer 10 should have an outside diameter that is roughly the same as the inside diameter of the perforated metal cylinder 42 in the front portion 14, and should be designed to fit into the perforated metal cylinder 42 at point 100.

The ported tube 56 is removable. When the tube 56 is installed, it is supported at the rear by a collar 102 that extends inward from the rear portion 16 of the housing 12 around the outlet 24. The collar 102 is similar to the collar 96 on the cover plate, which supports the front end of the ported tube 56. O-rings 104 and 106 are used to improve the acoustic seal between the collars and the ported tube. In particular, O-ring 104 is located in a groove 108 at the rear of the ported tube 56 and improves the acoustic seal between the collar 102 and the rear end of the tube 56. O-ring 106 is located in groove 110 at the front end of the tube 56 and improves the acoustic seal between the collar 96 and the front end of the tube 56.

The ported tube 56 can be easily removed by removing the cover plate 88 and sliding the tube 56 out of collar 102. An advantage of this arrangement is that the tube 56 can be replaced with another ported tube having different port dimensions, thus easily modifying the tuning of the active silencer.

As shown in FIG. 1, all electrical connections to the silencer 10 are made using a single socket connector 112. The preferred socket connector 112 is an 8-pin connector: four wires for transmitting speaker power, two wires for transmitting microphone signals and two wires for powering the microphones. (More wires may be needed for systems with more electrical components.) The socket connector 112 is attached to wires 114, 116 and 118 that transmit and receive electrical signals to and from an electronic controller 120 shown schematically in FIG. 1. Wire 114 is an input signal wire that transmits an input signal to the electronic controller 120. Wire 118 is an error signal wire that transmits an error signal to the controller 120. Two microphone power wires also accompany wires 114 and 118. Wires 116 are correction signal wires that transmits a correction signal from the electronic controller 120. Each speaker 60 and 62 has a pair of correction signal wires 116 (not shown) for transmitting speaker power. Each of the wires 114, 116 and 118 are located within a common conduit 122 that runs between the socket connector 112 and the controller 120.

The socket connector 112 connects or plugs into a socket 124. The socket 124 is electrically connected to the various electrical components within the silencer 10 that are necessary to operate the active silencer. As can be seen in FIG. 5, the socket 124 is attached through the rear portion 16 of the housing 12 so that wires 128, 130 and 133 attach to the socket 124 in the tuning chamber 64. The wires 128, 130, 133 correspond to wires 114, 116, and 118 with respect to number and function.

An error transducer 126 is positioned through the wall of the ported tube 56 downstream of the ports 68 and 70. The error transducer 126 is preferably a microphone, and senses sound propagating down the tube 56 downstream of the ports 68 and 70. The error microphone 126 transmits an error signal to the socket 124 through an error transducer wire 128.

An input transducer 134 is located in the front portion 14 of the housing 12. The input transducer 134 is preferably an input microphone that is mounted to sense sound flowing through the perforated metal cylinder 42. The input transducer 134 transmits an electrical signal through an input transducer wire 132 and an input terminal wire 133 to the socket 124. As shown in FIG. 2, the input terminal wire 133 is located within the rear portion 16 of the housing, and is physically separate from the input transducer wire 132 located in the front portion 14 of the housing. The input transducer wire 132 and the input terminal wire 133 communicate electrically through a terminal 136 that passes through the cover plate 88. Both the error transducer 126 and the input transducer 134 share power from the microphone power wires at the socket 124.

There are two pairs of wires 130 which are actuator wires 130 that electrically connect the speaker 60 and 62 to the socket 124. The actuator wires 130 pass through the speaker mounting plates 78. Silicone is used to seal around the actuator wires 130 at the point where they pass through the speaker mounting plate 78.

A second embodiment of an acoustic silencer 10A in accordance with the invention is shown in FIG. 7. The front 14 and rear 16 portions of the acoustic silencer 10A shown in FIG. 7 are preferably the same or similar as the corresponding components described in FIGS. 1 through 6. In FIG. 7, the outer housing 12 of the acoustic silencer 10A has a middle portion 138 in addition to the front 14 and rear 16 portions. The middle portion 138 of the outer housing 12 has a peripheral flange 140 extending outwardly at the front edge of the middle portion 138 of the housing 12. It is preferred that the flange 140 extend around the entire circumference of the middle portion 138 of the housing. The middle portion 138 of the housing also has a rear peripheral flange 140 extending outwardly from the middle portion 138 at the rear edge of the middle portion 138. It is preferred that the rear flange 142 extend around the entire circumference of the middle portion 138. Using nuts 30 and bolts 32 through the flanges, the middle portion 138 is attached to the front portion 14 and the rear portion 16 to form a single integral unit.

FIG. 7 shows a straight through passive silencer having a resonance chamber 144 located within the middle portion 138 of the housing. The straight through silencer in the middle portion 138 has an acoustically permeable cylinder 146 through which gas flows. The cylinder 146 is preferably a perforated metal cylinder having a diameter substantially the same as the inside diameter of the inlet 22. The straight through silencer in the middle portion also has a front plate 148 that supports the straight through cylinder 146 and also has a collar 150 that is similar to collar 98 shown in FIG. 2.

Another terminal 152 is positioned through the front plate 148. An extension wire 154 provides an electrical connection between terminals 136 and 152, thus completing the electrical connection necessary to transmit an input signal from the input transducer 134 to the socket 124.

Figure 8:
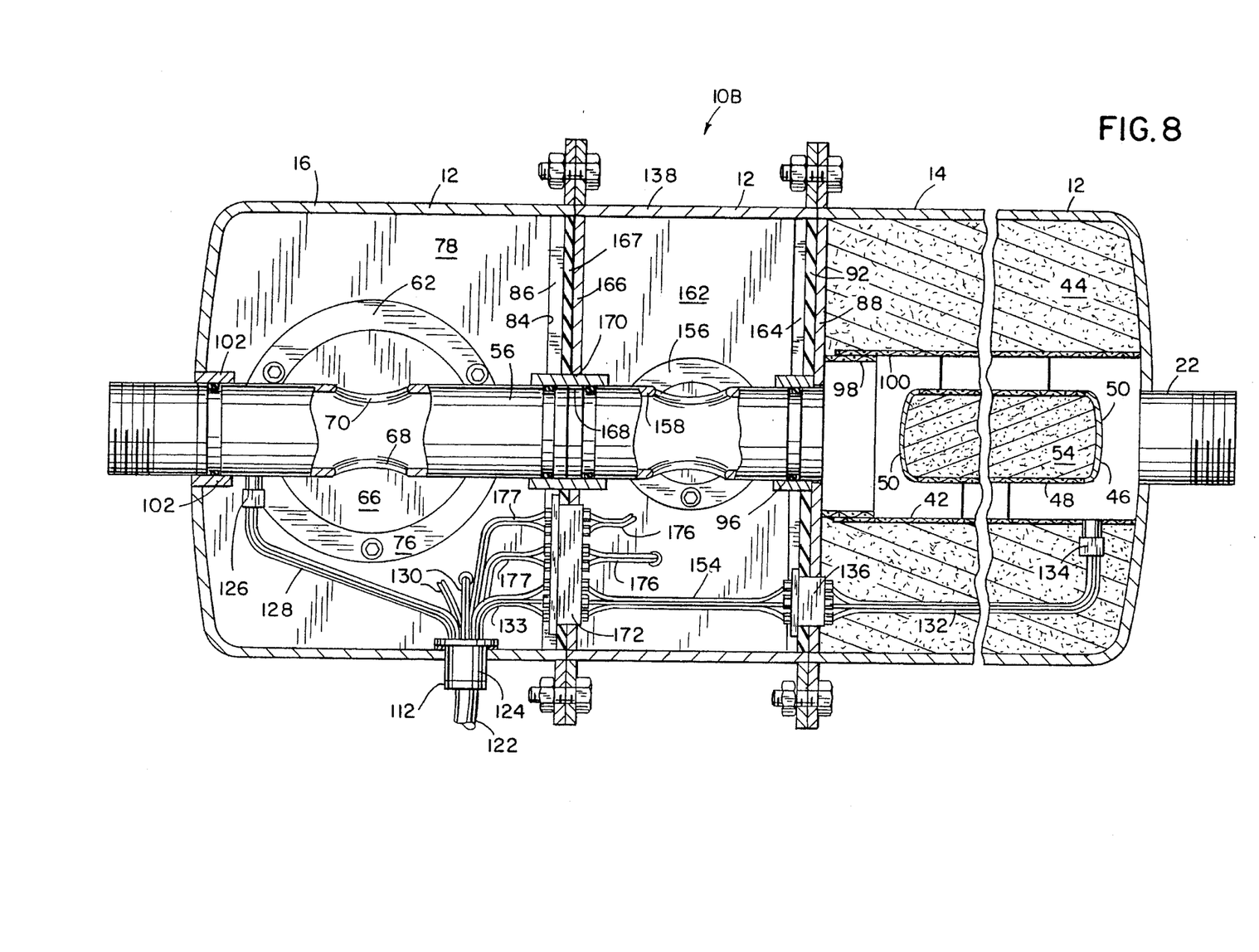
FIG. 8 is a longitudinal sectional view of yet another embodiment of an acoustic silencer made in accordance with the invention.

A third embodiment of an acoustic silencer 10B in accordance with the invention is shown in FIG. 8. The acoustic silencer 10B shown in FIG. 8 is similar to that shown in FIG. 7, except the embodiment shown in FIG. 8 has an active silencer within the middle portion 138 instead of a passive silencer. The front 14 and rear portions of the acoustic silencer 10B shown in FIG. 8 are preferably the same as the corresponding components described in FIGS. 1 through 6 except as otherwise noted herein. In FIG. 8, the acoustic silencer 10B has a speaker 156 in the middle portion 138 that is smaller than the speaker 62 in the rear portion 16. Such a configuration with a smaller speaker 156 in the middle portion 138 may be useful for improving the attenuation of middle frequency sound waves. The active silencer in the middle portion 138 uses a tuning chamber and a ported tube 158 in a manner similar to that described above with respect to the active section in the rear portion 16. For instance, the silencer in the middle portion has a mounting plate 162 and an enclosure plate 164 similar to mounting plate 78 and enclosure plate 86 shown in FIG. 2. Note that the cover plate 88 which is shown in FIG. 2 can now be used as a cover plate between the middle portion 138 and the front portion 14 in FIG. 8. A modified cover plate 166, however, is used between the tuning chamber in the rear portion 16 and the tuning chamber in the middle portion 138. A gasket 167 is provided that is similar to gasket 92.

The modified cover plate 166 has a hole 168 through which gas flows from the middle portion 138 into the rear portion 16. A collar 170 extends both forward and rearward around the hole 168 and is used to support both the ported tube 56 for the rear portion 16 and the ported tube 158 for the middle portion 138.

The modified cover plate 166 has a terminal strip 172. The terminal strip 172 passes through the cover plate 166. One terminal on the terminal strip 172 electrically connects extension wire 154 to the input terminal wire 133 connected to the socket 124. The other end of the extension wire 154 is connected to terminal 136 which is electrically connected to the input transducer wire 132 connected to the input transducer 134. Another terminal on the terminal strip 172 electrically connects wires between the socket 124 and the speakers 156 in the middle portion 138. A second actuator terminal wire 177 is located in the rear portion 16, and connects between the socket 124 and terminal 172. A second pair of actuator wires 176 for each speaker 156 is located in the middle portion 138, and connects terminal 172 to the speakers 156. The speakers 156 in the middle portion 138 are driven in unison like the speakers in the rear portion 16. The second actuator wires 176 for each speaker 156 pass through the speaker mounting plate 162 and silicone is used to seal the passage.

Having described the invention, many modifications thereto will be apparent to those skilled in the art without departing from the scope and spirit of the present invention. For instance, it is not necessary to use a tuning chamber in the active portions of the silencer. It is possible to use other types of passive silencers in either the front or middle portions. Also, it is contemplated that any of the portions, front, middle or rear, could contain a hybrid type of silencer such as that described in U.S. Pat. No. 4,665,549.

I claim:

1. An acoustic silencer for silencing an acoustic wave propagating through a pipe comprising:
   an outer housing with an inlet for receiving a gas flowing through a pipe and an outlet through which the gas exits the housing, the inlet being in a front portion of the housing and the outlet being in a rear portion of the housing;
   a passive silencer located in the front portion of the housing;
   an active silencer having a tube through which gas flows from the passive silencer to the outlet and an actuator for generating a canceling acoustic wave that is in acoustic communication with the gas in the tube through a port in the tube, the actuator and the tube being located in the rear portion of the housing.

2. An acoustic silencer as recited in claim 1 wherein the tube is removable from the rear portion of the housing.

3. An acoustic silencer as recited in claim 1 wherein the active silencer further comprises a tuning chamber in the rear portion of the housing and the actuator is in acoustic communication with the gas in the tube through the tuning chamber and the port in the tube.

4. An acoustic silencer as recited in claim 1 wherein the active silencer further comprises an input transducer located within a front portion of the housing.

5. An acoustic silencer as recited in claim 1 wherein the actuator is a speaker and the active silencer further comprises another speaker located in the rear housing portion, each speaker having a diaphragm which moves substantially perpendicular to the longitudinal axis of the tube and symmetrically opposite to the other diaphragm.

6. An acoustic silencer as recited in claim 5 wherein each speaker is mounted to the rear housing portion by a speaker mounting plate having a peripheral edge and a speaker hole therethrough, the speaker mounting plate being attached along part of the peripheral edge to the rear portion of the housing and the speaker being attached to the speaker mounting plate so that the diaphragm of the speaker is in acoustic communication with the gas in the tube through the port in the tube; and
   an enclosure plate is attached to the rear housing portion upstream of the speaker, and to the part of the peripheral edge of the speaker mounting plate that is not attached to the rear housing portion.

7. An acoustic silencer as recited in claim 5 wherein the tube has another port, and the ports are located opposite of one another and do not face the speaker diaphragms.

8. An acoustic silencer as recited in claim 2 wherein the removable tube is supported by a first collar adjacent to the outlet when the tube is installed.

9. An acoustic silencer as recited in claim 8 further comprising a cover plate that can be attached to the enclosure plate to separate the active silencer from the passive silencer, the cover plate having a hole therethrough and a second collar around the hole extending inwards towards the first collar for receiving and supporting the tube.

10. A system as recited in claim 9 wherein the tube has:
    a first circumferential groove on the end of the tube that is located within the first collar by the outlet when the tube is installed;
    a second circumferential groove around the other end of the tube that is located in the second collar on the cover plate when the tube is installed;
    a first O-ring that is located within the first groove; and
    a second O-ring that is located within the second groove.

11. An acoustic silencer as recited in claim 6 further comprising a rubber gasket that can be located between the enclosure plate and the cover plate.

12. An acoustic silencer as recited in claim 1 wherein the passive silencer has an acoustically permeable cylindrical wall located within the front housing portion;
    acoustically absorptive material packaged between the acoustically permeable wall in the front housing portion; and
    a bullet-like member support by spokes within the acoustically permeable cylinder.

13. An acoustic silencer as recited in claim 12 wherein the cross-sectional area of the space between the bullet-like member and the acoustically permeable cylinder is greater than or equal to the cross-sectional area of the inlet.

14. An acoustic silencer as recited in claim 6 wherein each speaker has a frame which supports the diaphragm and the speaker is attached to the speaker mounting plate by attaching the frame of the speaker to the side of the speaker mounting plate exposed to the ported tube, and the space between the speaker mounting plates is large enough so that each speaker can be removed from the speaker hole in the mounting plate when the tube is removed from the rear portion of the housing.

15. An acoustic silencer as recited in claim 1 wherein the outer housing further comprises a middle portion located between the front and rear portions of the housing, and another passive silencer is located in the middle housing portion.

16. An acoustic silencer as recited in claim 1 wherein the outer portion further comprises a middle portion located between the front and rear portions of the housing, and another active silencer is located in the middle housing portion.

17. An acoustic silencer as recited in claim 16 further comprising an error transducer located in the tube in the rear housing portion downstream of the port in the tube, wherein the error transducer generates an error signal that is used by both the active silencer in the rear housing portion and the active silencer in the middle housing portion.

18. An acoustic silencer as recited in claim 16 further comprising an input transducer located in the front portion of the housing that generates an input signal used by both the active silencer in the rear housing portion and the active silencer in the middle housing portion.

19. An active acoustic silencer for silencing an acoustic wave propagating through a pipe comprising:

an outer housing with an inlet for receiving a gas flow through said pipe and an outlet through which the gas exits the housing;

a tube within the housing through which gas flows for at least a portion of a flow path between the inlet and the outlet of the housing, the tube having a port therein and being removable from the housing;

an actuator for generating a canceling acoustic wave that is in acoustic communication with gas in the tube through the port in the tube;

wherein the removable tube is supported at one end by a first collar adjacent to the outlet and at the other end by a second collar when the tube is installed.

20. An active acoustic silencer as recited in claim 19 wherein the tube has:

a first circumferential groove on the end of the tube that is located within the first collar by the outlet;

a second circumferential groove around the other end of the tube that is located in the second collar;

a first O-ring that is located within the first groove; and a second O-ring that is located within the second groove.

21. An acoustic silencer for silencing an acoustic wave propagating through a pipe comprising:

an outer housing with an inlet for receiving a gas flowing through a pipe and an outlet through which the gas exits the housing, the inlet being in a front portion of the housing and the outlet being in a rear portion of the housing; the front portion of the housing being separable from the rear portion of the housing;

a passive silencer located in the front portion of the housing;

an active silencer having a tube through which gas flows from the passive silencer to the outlet, a port in the tube, an actuator for generating a canceling acoustic wave, and a tuning chamber in acoustic communication with the actuator and the port in the tube; wherein the tube, the actuator and the tuning chamber are located in the rear portion of the housing.

22. An acoustic silencer as recited in claim 21 wherein the active silencer further comprising an error transducer located in the tube downstream of the port in the tube.

23. An acoustic silencer as recited in claim 21 wherein the active silencer further comprises an input transducer located in the front portion of the housing.

24. An acoustic silencer as recited in claim 21 wherein the actuator is a speaker and the active silencer further comprises another speaker located in the rear housing portion, each speaker having a diaphragm facing the tuning chamber which moves substantially perpendicular to a longitudinal axis of the tube and is located symmetrically opposite to the other diaphragm.

25. An acoustic silencer as recited in claim 24 wherein each speaker is mounted to the rear housing portion by a speaker mounting plate having a peripheral edge and a speaker hole therethrough, the speaker mounting plate being attached along a part of the peripheral edge to the rear portion of the housing and the speaker being attached to the speaker mounting plate so that the diaphragm of the speaker is in acoustic communication with the tuning chamber; and an enclosure-plate is attached to the rear housing portion upstream of the speaker, and to the part of the peripheral edge of the speaker mounting plate that is not attached to the rear housing portion.

26. An acoustic silencer as recited in claim 24 wherein the tube has another port, and the ports are located opposite of one another and do not face the speaker diaphragms.

27. An acoustic silencer as recited in claim 25 wherein the tube is removable.

28. An acoustic silencer as recited in claim 27 wherein the tube is supported by a first collar adjacent to the outlet when installed, and the silencer further comprises a cover plate that can be attached to the enclosure plates to acoustically seal the tuning chamber, the cover plate having a hole therethrough and a second collar around the hole extending inward towards the tuning chamber for receiving and supporting the tube.

29. An acoustic silencer as recited in claim 28 wherein the tube has:

a first circumferential groove on the end of the tube that is located within the first collar by the outlet when the tube is installed;

a second circumferential groove around the other end of the tube that is located in the second collar on the cover plate when the tube is installed;

a first O-ring that is located within the first groove to acoustically seal the tuning chamber at the outlet; and a second O-ring that is located within the second groove to acoustically seal the tuning chamber by the end of the tube supported by the collar on the cover plate.

30. An acoustic silencer as recited in claim 28 further comprising a rubber gasket that can be located between the enclosure plates and the cover plate.

31. An acoustic silencer as recited in claim 21 wherein the passive silencer has an acoustically permeable cylindrical wall located within the front housing portion;

acoustically absorptive material packaged between the acoustically permeable wall and the front housing portion; and a bullet-like member supported by spokes within the acoustically permeable cylinder.

32. An acoustic silencer as recited in claim 31 wherein the cross sectional area of the space between the bullet-like member and the acoustically permeable cylinder is greater than or equal to the cross sectional area of the inlet.

33. An acoustic silencer as recited in claim 21 wherein the front portion of the housing has a flange extending radially outward from the housing on the end opposite of the inlet, the rear portion of the housing has a flange extending radially outward from the housing on the end opposite of the outlet, and the front and rear portions can attach together by pressing the flanges towards one another.

34. An acoustic silencer as recited in claim 27 wherein each speaker has a frame that supports the diaphragm and the speaker is attached to the speaker mounting plate by attaching the frame of the speaker to a side of the speaker mounting plate exposed to the tuning chamber, and the space in the tuning chamber between the speaker mounting plates is large enough so that each speaker can be removed from the speaker hole in the mounting plate through the tuning chamber when the tube is removed from the tuning chamber.

35. An acoustic silencer as recited in claim 21 wherein the outer housing further comprises a middle portion located between the front and rear portions of the housing which is also separable from the front and rear portions, and another passive silencer is located in the middle housing portion.

36. An acoustic silencer as recited in claim 21 wherein the outer housing further comprises a middle portion located between the front and rear portions of the housing which is also separable from the front and rear portions, and another active silencer is located in the middle housing portion.

37. An acoustic silencer as recited in claim 36 further comprising an error transducer located in the tube in the rear housing portion downstream of the port in the tube, wherein the error transducer generates an error signal used by both the active silencer in the rear housing portion and the active silencer in the middle housing portion.

38. An acoustic silencer as recited in claim 36 further comprising an input transducer located in the front portion of the housing that generates an input signal used by both the active silencer in the rear housing portion and the active silencer in the middle housing portion.

39. An acoustic silencer as recited in claim 21 wherein the port has a length that is equal to the thickness of the tube.

40. An acoustic silencer as recited in claim 27 wherein the port has a length that is equal to the thickness of the tube.

41. An acoustic silencer for silencing an acoustic wave propagating through a pipe comprising:
    an outer housing with an inlet for receiving a gas flowing through a pipe and an outlet through which the gas exits the housing, the inlet being located in a front portion of the housing and the outlet being located in a rear portion of the housing, the front portion of the housing being separable from the rear portion of the housing;
    a passive silencer located in the front portion of the housing;
    an active silencer having an actuator for generating a canceling acoustic wave, the actuator being located in the rear portion of the housing, and an error transducer located in the rear portion of the housing downstream of the actuator, the error transducer generating an error signal;
    an electronic controller located outside of the outer housing that receives the error signal and generates a correction signal that drives the actuator;
    a socket located in the rear housing portion, an error transducer wire connecting the error transducer to the socket and an actuator wire connecting the actuator to the socket; and
    a socket connector electrically connected to an error signal wire that is connected to the electronic controller for transmitting the error signal, the socket connector also being electrically connected to a correction signal wire that is electrically connected to the electronic controller for transmitting the correction signal;
    wherein the socket connector can engage the socket so that the error signal can be transmitted from the error transducer to the electronic controller and the correction signal can be transmitted from the electronic controller to the actuator.

42. An acoustic silencer as recited in claim 41 further comprising:
    an input transducer located in the front portion of the housing;
    a terminal that provides an electrical connection between the front portion and the rear portion of the housing;
    an input transducer wire electrically connecting the input transducer to the terminal;
    an input terminal wire electrically connecting the terminal to the socket; and
    an input signal wire that is electrically connected to the socket connector and the electronic controller for transmitting an input signal to the electronic controller.

43. An acoustic silencer as recited in claim 42 wherein the outer housing further comprising a middle portion located between the front and rear portions of the housing that is also separable from the front and rear portions and the silencer has another terminal and an extension wire that can be connected between the terminals to provide an electrical connection from the front portion to the rear portion of the housing.

44. An acoustic silencer as recited in claim 43 wherein a second actuator for a second active silencer is located in the middle portion of the housing, and the silencer has:
    an actuator terminal that provides an electrical connection between the rear portion and the middle portion of the housing;
    a second actuator wire electrically connecting the second actuator to the actuator terminal;
    an actuator terminal wire electrically connecting the actuator terminal to the socket; and
    a second correction wire that is electrically connected between the electronic controller and the socket for transmitting a second correction signal.

* * * * *

UNITED STATES PATENT AND TRADEMARK OFFICE
CERTIFICATE OF CORRECTION

PATENT NO. : 5,513,266
DATED : April 30, 1996
INVENTOR(S) : Michael T. Zuroski

It is certified that error appears in the above-indentified patent and that said Letters Patent is hereby corrected as shown below:

CLAIM 25, Col. 12, Line 28, after "enclosure" and before "plate" delete "-".

Signed and Sealed this

Sixteenth Day of July, 1996

Attest:

BRUCE LEHMAN

Attesting Officer

Commissioner of Patents and Trademarks